United States Patent [19]  [11] 3,995,028
Ōmura et al.  [45] Nov. 30, 1976

[54] ANTIBIOTIC OS-3256-B

[75] Inventors: Satoshi Ōmura; Iwao Umezawa, both of Tokyo; Keiki Satoh, Chiba; Juichi Awaya, Soka; Kanki Komiyama, Chofu; Ruiko Oiwa, Yokohama, all of Japan

[73] Assignee: The Kitasato Institute, Tokyo, Japan

[22] Filed: Aug. 21, 1975

[21] Appl. No.: 606,687

[52] U.S. Cl. .............................. 424/118; 195/80 R
[51] Int. Cl.² .......................................... A61K 35/74
[58] Field of Search ................... 424/118; 195/80 R

[56]  References Cited
OTHER PUBLICATIONS
Derwent Farmpol No. 70217v 40, Abstracting JA 095234, Published May 15, 1974.

Primary Examiner—Jerome D. Goldberg
Attorney, Agent, or Firm—Wolder & Gross

[57]  ABSTRACT

The present invention relates to a new antibiotic designated as OS-3256-B. OS-3256-B exhibits excellent inhibitory activities against animal tumors such as leukemia L-1210, Sarcoma-180 and Hela cells and gram-positive bacteria and is classified into the diazocompounds group. However, chromatographic analysis, Rf value and other experimental data reveal that OS-3256-B is a new compound of the type of azaamino acid derivatives. The present invention also provides a process for producing OS-3256-B by fermentation, in which OS-3256-B is produced by culturing a microorganism belonging to *Streptomyces candidus* var. azaticus in a culture medium conventionally used for culturing Streptomyces strain microorganisms.

1 Claim, 2 Drawing Figures

ANTIBIOTIC OS-3256-B

BACKGROUND OF INVENTION

Alazopeptin i.e. L-alanyl-(6-diazo-5-oxo)-L-norleucyl-(6-diazo-5-oxo)-L-norleucine is a known antibiotic having an inhibitory activity against animal tumors such as leukemia L-1210, Sarcoma-180 and Hela cells, and can be produced by fermentation of a microorganism belonging to Streptomyces. Alazopeptin has the molecular formula of $C_{15}H_{21}N_7O_6$ and the molecular weight of 413 and is believed to be a peptide consisting of one mole of alpha-alanine and two moles of a $C_6$ diazo keto amino acid. Preferable strains are exemplified by Streptomyces griseoplanus as reported by De Voe et al [Antibiotic Annual, 7, page 730 (1956)] and Streptomyces candidus var. azaticus by some of the present inventors and their partners [J. Antibiotics, 26, pages 181–183 (1973)]. It has now unexpectedly been discovered that a new substance which exhibits inhibitory activities against animal tumors such as leukemia L-1210, Sarcoma-180 and Hela cells and gram-positive bacteria can be obtained by culturing a microorganism belonging to Streptomyces candidus var. azaticus.

DETAILED DESCRIPTION OF INVENTION

An object of the present invention is to provide a new antibiotic having inhibitory activities against animal tumors such as leukemia L-1210, Sarcoma-180 and Hela cells and gram-positive bacteria, said new antibiotic is designated as OS-3256-B in the present specification.

Another object of the present invention is to provide a process for producing OS-3256-B by fermentation.

Other objects and features will be apparent from a reading of the following specification.

Figure 1:
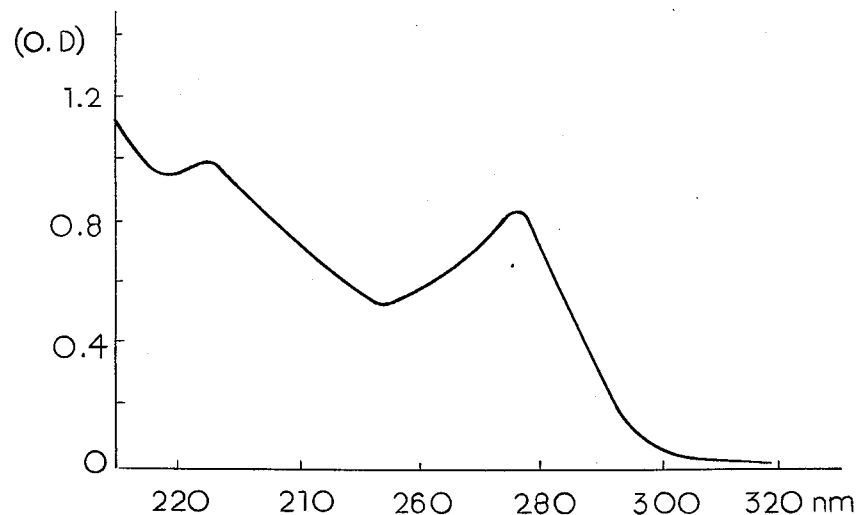
FIGS. 1 and 2 show the UV and IR absorption, respectively, of the OS-3256-B product of the present invention.

New antibiotic OS-3256-B provided according to the present invention has the following characteristics.

I. Physical and Chemical Characteristics a. Physical state:
White amorphous powder which is hygroscopic and is very unstable to heat.

b. Melting point and decomposing point:
Indefinite; Decomposes with moist air gradually in a wide temperature range.

c. Elemental analysis:
C = 46.77%, H = 5.99%, N = 18.12% d. Molecular weight and formula:
OS-3256-B has the following assumptive formula: $C_{14-15}H_{22-24}N_{5-6}O_{6-7}$. Because of the very weak stability to heat of OS-3256-B, its molecular weight and formula can hardly be determined even by means of mass spectrum and other procedures. The above-mentioned assumptive formula is obtained by elemental analysis, refractory index and other experimental data.

e. Nature:
Amphoteric compound f. Chromatographic mobility:
Shown in Table 1 where Rf values are determined by bioautography against *Bacillus subtilis*, although ninhydrin may also be used for the determination.

Table 1

| | Solvent System | Rf |
|---|---|---|
| Silica gel TLC | n-Butanol-methanol-water (2:1:3) | 0.56 |
| | n-Butanol-methanol-water (3:1:2) | 0.22 |
| | n-Butanol-acetic acid-water (3:1:2) | 0.31 |
| Avicel TLC | Ethanol-ammonia water-water (8:1:1) | 0.16 |
| | n-Butanol-acetic acid-water (3:1:2) | 0.46 |
| | n-Butanol-ethanol-water (2:2:3) | 0.55 |
| Paper chromatography | 93.8% n-Butanol-44% propionic acid (1:1) | 0.34 |
| | Ethanol-t-butanol-formic acid-water (60:20:5:15) | 0.50 |

Figure 2:
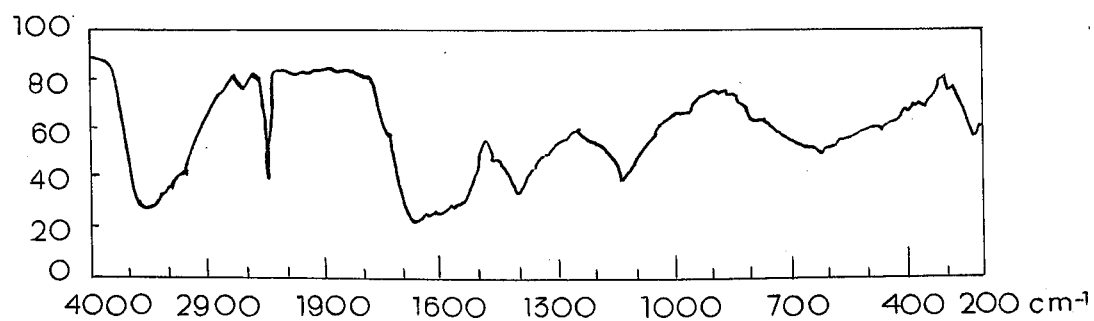

Note:
TLC - thin layer chromatography g. Ultraviolet absorption spectrum:
UV absorption maximum at 226 nm ($E_{1cm}^{1\%} = 394$) and 276 nm ($E_{1cm}^{1\%} = 310$) are found, as shown in FIG. 1.

h. Infrared absorption spectrum by using KBr tablet method:
The following frequency peaks are found, as shown in FIG. 2. 3300, 3050, 2900, 2150, 1660–1550, 1400, 1120 and 600 $cm^{-1}$ i. Solubility:
Insoluble in hexane, benzene, ethyl acetate, chloroform and acetone. Practically insoluble in methanol and ethanol. Soluble in aqueous methanol, aqueous ethanol, dimethyl sulfoxide. Freely soluble in water.

j. Color reaction:
Positive on ninhydrin and Rydon-Smith reagent k. Acid hydrolysis:
Acid hydrolysis of OS-3256-B with 6N-HCl yields alanine and the same with 6N-HCl after being oxidized with $HIO_4$ yields glutamic acid. In the former case, OS-3256-B is hydrolized with 6N-HCl at a temperature of 120° C for 2 hours and the hydrolysate is subjected to both the paper chromatography using a solvent system containing phenol, n-butanol, methylethyl ketone, propionic acid, acetone and water (20:20:50:10:10:20) and the cellulose chromatography using Avicel and a solvent system containing n-butanol, acetic acid and water (3:1:2) to confirm an alanine content. In the latter case, OS-3256-B is dissolved in 0.2M periodic acid, left at room temperature for 2 hours and is then hydrolized with 6N-HCl at a temperature of 120° C for 6 hours. The resultant hydrolysate is subjected to the paper chromatography using a solvent system containing pyridine, acetic acid and water (50:35:15) and the silica-gel thin-layer chromatography using a solvent system containing n-butanol, acetic acid and water (3:1:2) to confirm a glutamic acid content.

From the above-mentioned physical and chemical characteristics of OS-3256-B, it is apparent that OS-3256-B can be classified into a group of the diazocompounds exemplified by 6-diazo-5-oxo-L-norleucine; azaserine; duazomycins A, B and C; and alazopeptin. Hydrolysates of both OS-3256-B and alazopeptin indeed contain alanine and glutamic acid. However, OS-3256-B is unmistakably distinguishable from alazopeptin and represents a new antibiotic with respect to the following features.

a. UV and IR absorption spectra of OS-3256-B are different from those of alazopeptin.

b. On paper chromatograms, Rf values of OS-3256-B are distinguishable from those of alazopeptin, as shown in Table 2.

Table 2

Paper Chromatography of OS-3256-B and Azaamino Acid Group of Antibiotics

| Solvent System | I | II |
|---|---|---|
| Duazomycin A | 0.76 | 0.84 |
| Alazopeptin | 0.55 | 0.70 |
| DON | 0.40 | 0.40 |
| OS-3256-B | 0.34 | 0.50 |

Note:
I - 93.8% n-BuOH—44% propionic acid = 1:1
II - EtOH—t-BuOH—HCOOH—H$_2$O = 60:20:5:15

II. Biological Activities a. Antimicrobial spectrum:

Antimicrobial activities of the antibiotic by the agar dilution method are shown in Table 3 and those assayed on Davis' agar medium are shown in Table 4. OS-3256-B is active against *Staphylococcus aureus*, *Sarcina letea* and *Escherichia coli* NIHJ in the concentration of 25-50 mcg/ml, but less active against most of the gram-negative bacteria and fungi.

Table 3

Antimicrobial Spectrum of OS-3256-B

| Test Organism | Minimum inhibitory concentration (mcg/ml) |
|---|---|
| Bacillus subtilis PCI 219 | >100 |
| Staphylococcus aureus FDA 209P | 25 |
| "JC-1 | 25 |
| Sarcina lutea PCI 1001 | 25 |
| Mycobacterium smegmatis ATCC 607 | >100 |
| Escherichia coli NIHJ | 50 |
| "JC-2 | >100 |
| Klebsiella pneumoniae | >100 |
| Salmonella typhimurium | >100 |
| Xanthomonas oryzae | >100 |
| Candida albicans | >100 |
| Saccharomyces sake | 100 |
| Aspergillus niger | >100 |
| Trichophyton interdigitale | 100 |

Table 4

| Test Organism | MIC (μg/ml) |
|---|---|
| Bacillus subtilis PCI 219 | 1.56 |
| Escherichia coli JC-2 | 5.12 |

Note:
MIC - Minimum inhibitory concentration b. Effect on Leukemia L-1210:

Leukemia L-1210 cells were carried intraperitoneally in CDF$_1$ strain mice. Ascites tumor cells were counted in a hemocytometer and diluted in Hank's balanced salt solution to 1 × 10$^6$ cells/ml CDF$_1$ strain mice weighing 19–22 g received 0.1 ml injections of tumor cell suspension intraperitoneally. The antibiotic is dissolved in sterilized distilled water. Treatments are begun 24 hours after tumor inoculation. The effects of the antibiotic on the survival time of mice are presented in Table 5. When 9 mg/kg/day of the antibiotic is injected once daily for 10 days, the highest survival ratio of leukemic mice is obtained, and this is followed closely by 4.5 mg/kg/day. When large doses of the antibiotic, 28.6 or 18 mg/kg/day, are injected for 4 days, the survival effect is reduced as compared with the daily treatment with small doses for 10 days.

Table 5

Effect of OS-3256-B on Leukemia L-1210

| Dose (mg/kg/day) | Route and Regimen | Survival days Median | Range | Survival ratio (T/C %) |
|---|---|---|---|---|
| None | — | 7.6 | 7–8 | 100 |
| 9.0 | ip, day 1–10 | 14.6 | 9–16 | 192.1 |
| 4.5 | " | 14.4 | 14–15 | 189.5 |
| 2.3 | " | 11.8 | 11–13 | 155.3 |
| 1.2 | " | 9.8 | 9–10 | 128.9 |
| 0.6 | " | 8.4 | 8–9 | 110.5 |
| 28.6 | ip, day 1–4 | 13.2 | 13–14 | 173.7 |
| 18.0 | " | 13.0 | 12–14 | 171.1 |

Note:
Groups of 5 mice are inoculated with 10$^5$ L-1210 cells ip on day 0. The LD$_{50}$ of Os-3256-B is more than 150 mg/kg (ip).

c. Effect on Sarcoma-180:

A small piece (about 2 mm$^3$) of sarcoma-180 solid tumor is inoculated subcutaneously into the axillar region of dd-type strain mice weighing 20-22 g/ Treatments once daily for 10 days are begun 1 or 5 days after tumor inoculation. When 3.1–12.5 mg/kg/day of the antibiotic is given from one day after tumor inoculation, almost complete inhibition of tumor growth is observed until 1–2 weeks after the final injection. After this, a remarkable tumor growth begins in most of the animals treated with 6.3 or 12.5 mg/kg/day, whereas a complete inhibition and longer survival are observed in 4 out of 5 animals treated with 3.1 mg/kg/day. When the treatment is started five days after tumor inoculation, a strong inhibitory effect on tumor growth is also observed with 3.1 – 12.5 mg/kg/day. At a dose of 3.1 mg/kg/day, 4 out of 5 animals are alive for at least 70 days without tumor, and this is followed by 12.5 mg/kg/day (3 out of 5 animals).

d. Effect on Hela Cells:

A stock of Hela cells is grown in Eagle's minimum essential medium supplemented with 10% calf serum. After 48 hours of cultivation of Hela cells (1 × 10$^5$ ml) in Leighton tubes each inserted with a coverslip, the antibiotic dissolved in the growth medium is added to the tube. Morphlogical changes of Hela cells are observed under a light microscope after 72 hours cultivation from the addition of the antibiotic. With this result, shrinkage and decreasing numbers of nucleoli are observed, but no remarkable morphological change of nuclei is observed at concentrations of 500 – 62.5 mcg/ml. An inhibition of mitosis is observed at a concentration of 31.5 mcg/ml. These findings indicates that OS-3256-B mainly affects nucleoli of Hela cells.

According to another aspect of the present invention, there is provided a process for producing a new antibiotic OS-3256-B by fermentation, characterized by culturing a microorganism which belongs to Streptomyces and which is capable of producing OS-3256-B in a culture medium containing carbon source and nitrogen source under aerobic conditions to accumulate OS-3256-B in the culture broths and recovering the accumulated OS-3256-B therefrom.

Preferable strains which may be used for the purpose of the present invention include Streptomyces candidus and mutant strains thereof so long as they are capable of producing OS-3256-B by fermentation. However, an especially advantageous result can be obtained by culturing *Streptomyces candidus* var. azaticus (FERM-P No. 1608) which is freely available from Fermentation Research Institute, Agency of Industrial Science and Technology, Japan. Some of the present inventors and their associates reported in Journal of Antibiotics, 7, pages 181–183 (1973) that alazopeptin could be produced by culturing this strain in a culture medium.

The fermentation according to the present invention is carried out aerobically with shaking and/or submerged conditions at a temperature of from 15° to 40° C at a pH of from 3 to 10, and it is preferred to carry out the fermentation at a temperature of from 25° to 35° C at a pH of from 5 to 8 for from 1 to 4 days, whereby a substantial amount of OS-3256-B is accumulated in the culture broths.

Any synthetic or organic medium may be used for the process of the present invention when the medium is adaptable for culturing the strains belonging to Streptomyces and when it contains a suitable amount of carbon source, nitrogen source and inorganic substances. It is also possible to add various nutrients which are used to promote the growth of the strain in use.

The useful carbon sources are more concretely exemplified by glucose, starch, glycerine and the like, and the concentration of the carbon source is preferably from 0.5 to 5.0% when calculated as glucose based upon the medium. It is also possible to use organic acids such as for example gluconic acid, acetic acid and various amino acids such as alanine and glutamic acid.

As the nitrogen source, it is possible to use, for example, ammonia, various organic and inorganic ammonia salts such as chloride, sulfate, phosphate and nitrate of ammonia, nitrogen-containing organic materials such as urea, peptone, meat extract, soybean meal, corn steep liquor, fish meal and the like. It is understood that these carbon sources, nitrogen sources and inorganic substances include those used conventionally for fermentation of microorganisms belonging to Streptomyces.

After completion of the fermentation, OS-3256-B accumulated in the cultured broths can be isolated, for example, by filtering the broths, followed by treating the filtrate with a suitable adsorbent such as active carbon, ion-exchange resin and the like which are conventionally used for the separation of various antibiotic substances. In one embodiment using a microorganism capable of producing OS-3256-B by fermentation such as Streptomyces candidus var. azaticus FERM-P No. 1608, the filtrate is adsorbed onto a column packed with active carbon. The column is eluted with an aqueous organic solvent such as aqueous ethanol, aqueous methanol and aqueous acetone, whereby the desired antibiotic followed by alazopeptin is successively eluted. The active fractions are combined, concentrated and freeze-dried to obtain a crude product. The crude product is subjected to the column-chromatography using for example silica-gel, Avicel (trademark for microcrystalline cellulose manufactured by FMC Corporation, American Viscose Division, U.S.A.), Sephadex G-10 (trademark for a synthetic compound derived from polysaccharide dextran manufactured by Pharmacia Fine Chemicals Inc., U.S.A.) and the active fractions are collected, combined, freeze-dried to obtain the desired product in the form of white amorphous powder.

The following non-limitative examples illustrate the present invention.

EXAMPLE 1

Streptomyces candidus var. azaticus (FERM-P No. 1608) was cultured at a temperature of 27° C for 30 hours with aeration (15 l/min) and agitation (250 rpm) in a 30-liter jar fermentor containing a culture medium adjusted to pH 7 and having a composition of glycerol (2%), soybean meal (2%), meat extract (0.3%) and sodium chloride (0.3%). After completion of the cultivation, the culture broths (20 liters) were filtered and passed through a column packed with active carbon (1 liter). The column was washed with water (5 liters) and the new antibiotic followed by alazopeptin were successively eluted with 20% aqueous acetone. The active fractions of OS-3256-B were concentrated in vacuo and added with methanol. After removing the precipitate, the supernatant was concentrated in vacuo and acetone was added. The precipitate formed was collected, dissolved in water, passed through a column packed with silica-gel (500 ml; Kieselgel 60 Merck) and then eluted with water. To obtain a crude powder, the active fractions were concentrated in vacuo and freeze-dried. This crude powder was dissolved in a mixture of ethanol — 20% ammonia water — water (8:1:1), passed through a column packed with Avicel (500 ml) prepared with the mixed solvent and then eluted with the same solvent. The active fractions were concentrated to remove the solvent and the aqueous solution of the crude antibiotic was passed through a column packed with 100 ml Sephadex G-10 and eluted with water. The fractions were checked by paper chromatography using a solvent system containing 93.8% aqueous n-butanol - 44% aqueous propionic acid (1:1) for distinguishing OS-3256-B from alazopeptin. The Rf value of the antibiotic was 0.34 on a bioautogram using *Bacillus subtilis* PCI-219 as the test microorganism. After concentrating, the aqueous solution of the antibiotic was freeze-dried to obtain 12 mg of OS-3256-B in the form of white amorphous powder.

EXAMPLE 2

20 Liters of a culture medium (pH - 7) having a composition of starch (2%), soybean meal (2%), meat extract (0.2%) and sodium chloride (0.3%) was placed in a 30-liter jar fermentor, to which the same strain as that used in Example 1 was inoculated and cultured at a temperature of 28° C for 50 hours with aeration (10 l/min) and agitation (200 rpm). After completion of the cultivation, the cultured broths were filtered. The filtrate (18 liters) was passed through a column packed with active carbon (400 g) to adsorb effective composition onto the column. The column was washed with desalted water (6 liters) and eluted with 20% aqueous acetone. The active fractions (1000 ml) of OS-3256-B were concentrated and then methanol was added. After removing the precipitate, the supernatant was freeze-dried to obtain yellowish white powder (2.0 g). The powder was passed through a column packed with silica-gel (60 g), and eluted with water. The active fractions (50 ml) which were checked in a similar manner to that described in Example 1 were concentrated in vacuo to give white powder (500 mg). This powder was dissolved in a solvent of ethanol - ammonia water - water (8:1:1), passed through a column packed with Avicel (20 g) prepared with the same solvent, and the active fractions (each 5 ml) were eluted with the same solvent. The active fractions (30 ml) were collected, combined and freeze-dried to give white powder (20 mg). The powder was dissolved in desalted water (1 ml), passed through a column packed with 60 ml Sephadex G-10, and eluted with desalted water. The active fractions (8 ml; Fractions Nos. 46-49) were freeze-dried to obtain 2.5 mg of OS-3256-B in the form of a white powder.

EXAMPLE 3

20 Liters of a culture medium (pH - 7) having a composition of glycerol (2%), soybean meal (2%), meat extract (0.2%) and sodium chloride (0.3%) was placed in a 30-liter jar fermentor, to which the same strain as that used in Example 1 was inoculated and cultured at a temperature of 28° C for 2 days with aeration (10 l/min) and agitation (200 rpm). After completion of the cultivation, the cultured broths were filtered. The filtrate (18 liters) was passed through a column packed with active carbon (400 g) to adsorb effective composition onto the column. The column was washed with desalted water (6 liters) and eluted with 20% aqueous acetone. The active fractions were checked in a similar manner to that described in Example 1. The combined active fractions (500 ml) of OS-3256-B which gave a single spot were concentrated and then methanol was added. After removing the precipitate, the supernatant was freeze-dried to obtain yellow powder (7.2 g). The powder was then dissolved in 20% methanol, passed through a column packed with active carbon (50 g), eluted with 20% methanol (3000 ml) to remove impurities and further eluted with 20% acetone. The active fractions (200 ml) were combined and concentrated in vacuo to remove the acetone and were then freeze-dried to obtain 0.75 g of crude OS-3256-B in the form of white-yellowish powder.

What is claimed is:

1. Antibiotic OS-3256-B having the following physical and chemical characteristics:
    a. Physical state: White amorphous powder which is hygroscopic and very unstable to heat;
    b. Melting and decomposing points: Indefinite
    c. Elemental analysis: C = 46.77%, H = 5.99%, N = 18.12%
    d. Molecular weight and formula (assumptive): $C_{14-15}H_{22-24}N_{5-6}O_{6-7}$
    e. Nature: Amphoteric compound
    f. Chromatographic mobility determined by bioautography against *Bacillus subtilis*:

| | Solvent System | Rf |
|---|---|---|
| Silica gel TLC | n-Butanol-methanol-water (2:1:3) | 0.56 |
| | n-Butanol-methanol-water (3:1:2) | 0.22 |
| | n-Butanol-acetic acid-water (3:1:2) | 0.31 |
| Avicel TLC | Ethanol-ammonia water-water (8:1:1) | 0.16 |
| | n-Butanol-acetic acid-water (3:1:2) | 0.46 |
| | n-Butanol-ethanol-water (2:2:3) | 0.55 |
| Paper chromatography | 93.8% n-Butanol-44% propionic acid (1:1) | 0.34 |
| | Ethanol-t-butanol-formic acid-water (60:20:5:15) | 0.50 |

TLC — thin layer chromatography g. Ultraviolet absorption spectrum: UV absorption maximum at 226 nm ($E_{1cm}^{1\%} = 394$) and 276 nm ($E_{1cm}^{1\%} = 310$), as shown in FIG. 1;
h. Infrared absorption spectrum by KBr tablet method: Frequency peaks at 3300, 3050, 2900, 2150, 1660–1550, 1400, 1120 and 600 $cm^{-1}$, as shown in FIG. 2;
i. Solubility: Insoluble in hexane, benzene, ethyl acetate, chloroform and acetone, Practically insoluble in methanol and ethanol, Soluble in aqueous methanol, aqueous ethanol, and dimethyl sulfoxide, Freely soluble in water;
j. Color reaction: Positive on ninhydrin and Rydon-Smith reagent
k. Acid hydrolysis: Acid hydrolysis with 6N-HCl yields alanine, and acid hydrolysis with 6N-HCl subsequent to oxidation with $HIO_4$ yields glutamic acid.

* * * * *